United States Patent
Khan

(10) Patent No.: US 11,805,981 B2
(45) Date of Patent: Nov. 7, 2023

(54) APPARATUS FOR HOLDING AN ENDOSCOPE

(71) Applicant: Mubarak Muhamed Khan, Pune (IN)

(72) Inventor: Mubarak Muhamed Khan, Pune (IN)

(73) Assignee: Mubarak Muhamed Khan

( * ) Notice: Subject to any disclaimer, the term of this patent is extended or adjusted under 35 U.S.C. 154(b) by 101 days.

(21) Appl. No.: 17/604,759

(22) PCT Filed: Jul. 19, 2019

(86) PCT No.: PCT/IB2019/056195
§ 371 (c)(1),
(2) Date: Oct. 19, 2021

(87) PCT Pub. No.: WO2020/240270
PCT Pub. Date: Dec. 3, 2020

(65) Prior Publication Data
US 2022/0175227 A1    Jun. 9, 2022

(30) Foreign Application Priority Data

May 31, 2019  (IN) .............................. 201921021758

(51) Int. Cl.
*A61B 1/00*  (2006.01)
*A61B 90/57*  (2016.01)
*F16M 11/20*  (2006.01)
*F16M 13/02*  (2006.01)

(52) U.S. Cl.
CPC .......... *A61B 1/00149* (2013.01); *A61B 90/57* (2016.02); *F16M 11/2078* (2013.01); *F16M 13/022* (2013.01); *A61B 2090/571* (2016.02)

(58) Field of Classification Search
CPC .... A61B 90/50; A61B 90/57; F16M 11/2078; F16M 11/24
USPC ......................................................... 248/560
See application file for complete search history.

(56) References Cited

U.S. PATENT DOCUMENTS

| 8,216,125 B2 * | 7/2012 | Wilson | A61B 90/57 600/102 |
| 11,464,404 B2 * | 10/2022 | Altamura | A61B 17/42 |
| 2006/0259018 A1 * | 11/2006 | Shilkrut | F16M 13/022 606/1 |

(Continued)

FOREIGN PATENT DOCUMENTS

| DE | 102004050714 A1 | 4/2006 |
| EP | 2495462 B1 | 8/2018 |
| JP | 2001145634 A * | 5/2001 |

(Continued)

*Primary Examiner* — Todd M Epps
(74) *Attorney, Agent, or Firm* — Jason C. Cameron

(57) ABSTRACT

An apparatus for holding an endoscope is disclosed. The apparatus includes a vertical arm mounted on a platform, a gas spring arm unit moves up and down in a space when fitted on a movable horizontal arm, a connecting means configured to lock the position of gas spring arm unit and the horizontal arm in order to obtain a predetermined position of the endoscope using one or more screws, a rail slider configured to move the endoscope in forward and backward direction in the space, a clamping unit configured to hold the endoscope by one of a clamp and a holding tube, wherein the vertical arm is configured to support the apparatus for holding the endoscope.

10 Claims, 1 Drawing Sheet

(56) References Cited

U.S. PATENT DOCUMENTS

2016/0256158 A1    9/2016  Whitfield et al.
2022/0225863 A1*   7/2022  Adler .................... A61B 90/57

FOREIGN PATENT DOCUMENTS

WO       2016075241 A1    5/2016
WO    WO-2021026229 A1 *  2/2021   ............ A61B 90/50

* cited by examiner

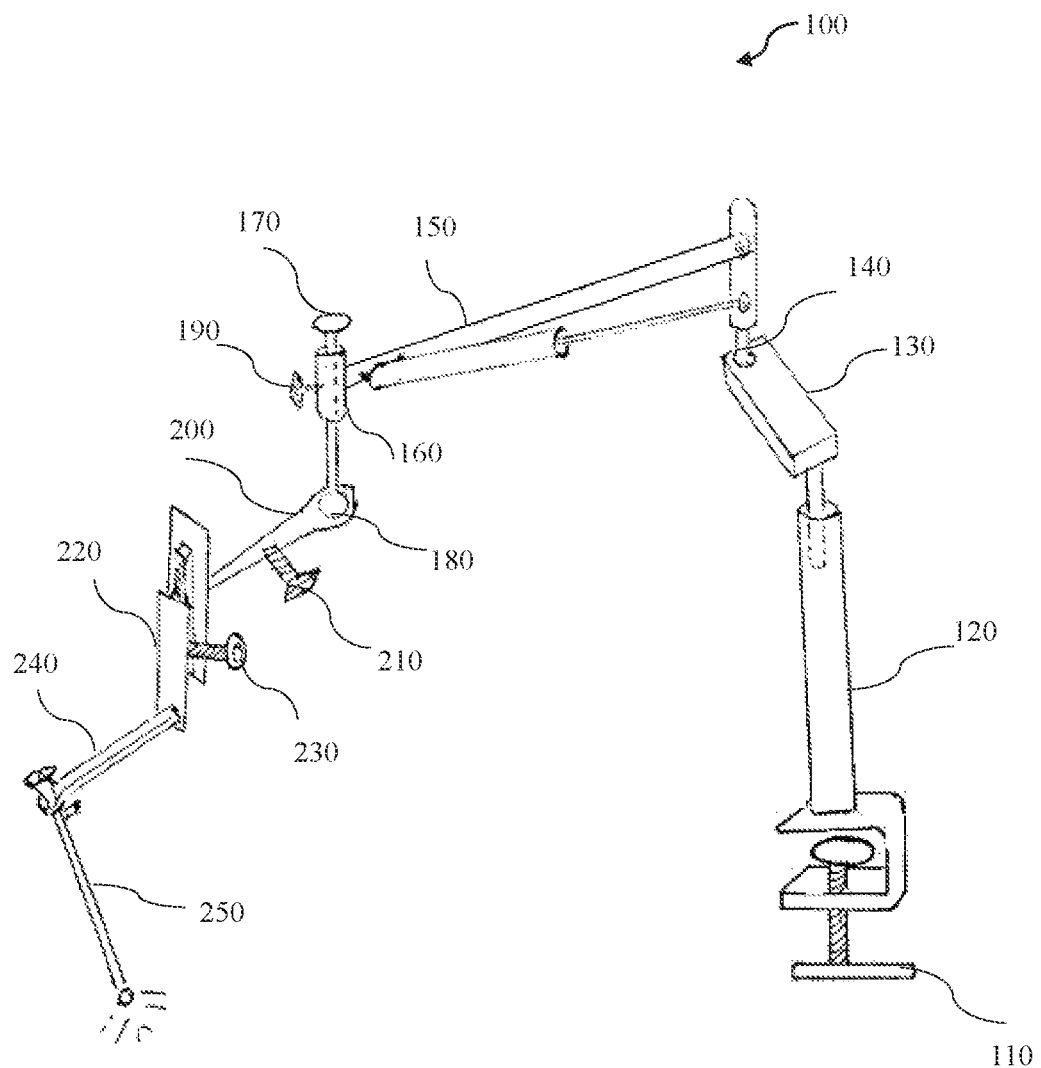

APPARATUS FOR HOLDING AN ENDOSCOPE

CROSS-REFERENCE TO RELATED APPLICATION

This National Phase Application claims priority from a complete patent application filed in India having Patent Application No. 201921021758, filed on May 31, 2019, and titled "AN APPARATUS FOR HOLDING AN ENDOSCOPE".

FIELD OF INVENTION

Embodiments of a present disclosure relate to a medical device, and more particularly to an apparatus for holding an endoscope.

BACKGROUND

A medical device is a device used for medical purposes. Endoscope is one of the medical devices used to examine the interior part of the body. During surgery, a doctor needs to hold the endoscope in one hand and perform surgery by other hand. However, holding the endoscope for a long-time during operation sometimes creates difficulties.

At present, the holding device such as articulating magic arm, simple holder and the like is used to hold the endoscope at a fixed position. However, constant motion of the endoscope is required during endoscopic surgeries which needs to be done by the person manually, thereby performing surgery using such holding device is a difficult task and consumes a lot of time.

Hence, there is a need for an improved apparatus for holding an endoscope in order to address the aforementioned issues.

BRIEF DESCRIPTION

In accordance with an embodiment of the disclosure, an apparatus for holding an endoscope is disclosed. The apparatus includes a vertical arm mounted on a platform. The apparatus also includes a gas spring arm unit fitted over a horizontal arm, wherein the horizontal arm is operatively coupled to the vertical arm. The gas spring arm unit moves up and down in a space when fitted on a movable horizontal arm. The apparatus also includes a connecting means operatively coupled to the gas spring arm unit. The connecting means is configured to lock the position of gas spring arm unit and the horizontal arm in order to obtain a predetermined position of the endoscope using one or more screws. The apparatus also includes a rail slider operatively coupled to the connecting means. The rail slider is configured to move the endoscope in forward and backward direction in the space. The apparatus also includes a clamping unit operatively coupled to the rail slider. The clamping unit is configured to hold the endoscope by one of a clamp and a holding tube, wherein the vertical arm is configured to support the apparatus for holding the endoscope.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended FIGURES.

BRIEF DESCRIPTION OF DRAWINGS

The disclosure will be described and explained with additional specificity and detail with the accompanying FIGURES in which:

FIG. 1 is a schematic representation of an apparatus for holding an endoscope in accordance with an embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the FIGURES by conventional symbols, and the FIGURES may show only those specific details that are pertinent to understanding the embodiments of the present disclosure so as not to obscure the FIGURES with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure.

The terms "comprise". "comprising", or any other variations thereof, are intended to cover a non-exclusive inclusion, such that a process or method that comprises a list of steps does not include only those steps but may include other steps not expressly listed or inherent to such a process or method. Similarly, one or more devices or sub-systems or elements or structures or components preceded by "comprises . . . a" does not, without more constraints, preclude the existence of other devices, sub-systems, elements, structures, components, additional devices, additional sub-systems, additional elements, additional structures or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

Embodiments of the present disclosure relate to an apparatus for holding an endoscope. The apparatus includes a vertical arm mounted on a platform. The apparatus also includes a gas spring arm unit fitted over a horizontal arm, wherein the horizontal arm is operatively coupled to the vertical arm. The gas spring arm unit moves up and down in a space when fitted on a movable horizontal arm. The apparatus also includes a connecting means operatively coupled to the gas spring arm unit. The connecting means is configured to lock the position of gas spring arm unit and the horizontal arm in order to obtain a predetermined position of the endoscope using one or more screws. The apparatus also includes a rail slider operatively coupled to the connecting means. The rail slider is configured to move the endoscope in forward and backward direction in the space. The apparatus also includes a clamping unit operatively coupled to the rail slider. The clamping unit is configured to hold the endoscope by one of a clamp and a holding tube, wherein the vertical arm is configured to support the apparatus for holding the endoscope.

FIG. 1 is a block diagram of an apparatus 100 for holding an endoscope 250 in accordance with an embodiment of the present disclosure. The apparatus 100 includes a vertical arm 120 mounted on a platform 110. In one embodiment, the vertical arm 120 may be made up of a metal. In one embodiment, the vertical arm may be mounted on an operating table. In another embodiment, the vertical arm 120 may be mounted on one of floor, ceiling and side walls of an operating room.

The apparatus 100 also includes a gas spring arm unit 150 fitted over a horizontal arm 130, wherein the horizontal arm 130 is operatively coupled to the vertical arm 120. The gas spring arm unit 150 moves up and down in space when fitted on a movable horizontal arm 130. In one embodiment, the gas spring arm unit 150 may include a fully adjustable gas spring articulating arm unit. In some embodiment, the horizontal arm 130 may be made up of the metal.

In one embodiment, the gas spring arm unit 150 may rotate in 360 degrees in a horizontal plane when fitted on the moveable horizontal arm 130. In some embodiment, a predetermined position for the gas spring arm unit 150 may be achieved by fixing a first screw 140 over the horizontal arm 130.

The apparatus 100 also includes a connecting means operatively coupled to the gas spring arm unit 150. The connecting means is configured to lock the position of the gas spring arm unit 150 and the horizontal arm 130 in order to obtain the predetermined position of the endoscope 250 using a second screw 190. In one embodiment, the connecting means may include a vertical rod 160. In one embodiment, the vertical rod 160 may be made up of the metal. In such embodiment, the vertical rod 160 may include a first ball 170 attached to the gas spring arm unit 150 and a second ball 180 attached to a horizontal rod 200. The first ball 170 of the vertical rod 160 may be configured to rotate the vertical rod 160 in 360 degrees in x-axis, y-axis and z-axis directions. The second ball 180 of the vertical rod 160 may be configured to fix the vertical rod 160 to achieve the predetermined position of the endoscope 250 by fixing the second screw 190.

In some embodiment, the horizontal rod 200 may include a socket 210. The socket 210 may be configured to achieve at least one of the x-axis, y-axis, z-axis direction in the space for attaining a required position of the endoscope 250. In one embodiment, the horizontal rod 200 may be made up of the metal.

Furthermore, the apparatus 100 also includes a rail slider 220 operatively coupled to the connecting means. The rail slider 220 is configured to move the endoscope 250 in forward and backward direction in the space. In one embodiment, the rail slider 220 may include a rack and pinion slider.

In one specific embodiment, the rail slider 220 may be configured to move the endoscope in the forward and backward direction mechanically with a pinion screw 230, wherein the pinion screw 230 is horizontally attached to an upper portion of the rail slider 220. In another embodiment, the rail slider 220 may be configured to move the endoscope in the forward and backward direction by motorised rail slider using one or more sensors.

Furthermore, the apparatus 100 also includes a clamping unit 240 operatively coupled to the rail slider 220. The clamping unit 240 is configured to hold the endoscope 250 by one of a clamp and a holding tube, wherein the vertical arm 120 is configured to support the apparatus 100 for holding the endoscope 250. As used herein, the term "clamp" is defined as a fastening device used to hold or secure objects tightly to prevent movement or separation through the application of inward pressure.

In one embodiment, the clamp may be a crab clamp with inner soft cushion of one of rubber and a silicon, wherein the clamp may be configured to hold the endoscope 250 of any diameter by one of neck and a shaft. In some embodiment, the holding tube may be configured to hold the endoscope 250 by a shaft. In such embodiment, the holding tube may be of variable length. In one embodiment, the holding tube may be made movable with the second ball of the vertical rod and the socket joint. In another embodiment, the holding tube may be fixed in desired position by tightening the screw.

In operation, the vertical arm 120 is mounted on an operation table 110 or either on one of a floor, ceiling and side walls of the operating room. Also, the vertical arm 120 is operatively coupled with the horizontal arm 130. The horizontal arm 130 rotates in 360 degree along x-axis, y-axis and z-axis directions. Also, upon reaching the required position of the vertical arm 120 and the horizontal arm 130 while rotating, the horizontal arm 130 is fixed by fixing the first screw 140. Further, the gas spring arm unit 150 is fitted on the horizontal arm 130 to move up and down in the space. Also, upon reaching the required position, the gas spring arm unit 150 is fixed by fixing the first screw in the horizontal arm 130. The length of the gas spring arm unit 150 is increased horizontally based on the movement of the horizontal arm 130.

Further, the vertical rod 160 with the first ball 170 rotates in 360 degrees along x-axis, y-axis and z-axis direction in space and is operatively coupled to the gas spring arm unit 150. Also, upon reaching the required position of the endoscope 250, the vertical rod 160 is fixed by fixing the second screw 190. Furthermore, the horizontal rod 200 holds the second ball 180 of the vertical rod 160. Also, the horizontal rod 200 includes a socket 210. The socket 210 and the second ball 180 achieve a plurality of motions in all directions to achieve required position of the endoscope 250.

Furthermore, upon achieving the required position for the endoscope 250 and required position is locked by fixing the second screw 190, the rail slider 220 which holds the endoscope 250 by clamping unit 240 and moves the endoscope 250 to and fro in space based on the rail slider 220 orientation in space in x-axis, y-axis and z-axis. Also, the rail slider 220 either moves the endoscope to and fro mechanically with a pinion screw 230 or motorizes with one or more sensors to achieve the required position of the endoscope 250.

Various embodiments of the present disclosure provide an adjustable endoscope holder. Also, the present disclosure provides a clamp for holding an endoscope which holds a varied size of endoscope from the neck. Moreover, the proposed apparatus provides a fully adjustable gas spring arm unit for doing the endoscope up and down during operation.

Further, the fully adjustable gas spring is fixed with a horizontal arm through a screw for achieving desired horizontal length and mobility during the operation. Furthermore, once the desired position of the endoscope is achieved during operation by moving the gas spring up and down, correspondingly the fine movement of endoscope can be achieved through the rail slider.

While specific language has been used to describe the disclosure, any limitations arising on account of the same are not intended. As would be apparent to a person skilled in the art, various working modifications may be made to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

I claim:

1. An apparatus for holding an endoscope comprising:
   a vertical arm mounted on a platform;
   a gas spring arm unit fitted over a horizontal arm, wherein the horizontal arm is operatively coupled to the vertical arm, wherein the gas spring arm unit moves up and down in a space when fitted on a movable horizontal arm;
   a connecting means operatively coupled to the gas spring arm unit, and configured to lock a position of the gas spring arm unit over the horizontal arm in order to obtain a predetermined position of the endoscope using one or more screws, wherein the connecting means comprises a vertical rod, wherein the vertical rod comprises:
   a first ball attached to the gas spring arm unit, wherein the first ball is configured to rotate the vertical rod up to 360 degrees in x-axis, y-axis and z-axis; and
   a second ball attached to a horizontal rod, wherein the second ball configured to fix the vertical rod to achieve predetermined position of the endoscope by fixing a second screw;
   a rail slider operatively coupled to the connecting means, and configured to move the endoscope in forward and backward direction in the space using one or more sensors; and
   a clamping unit operatively coupled to the rail slider, wherein the clamping unit is configured to hold the endoscope by one of a clamp and a holding tube, wherein the vertical arm is configured to support the apparatus for holding the endoscope.

2. The apparatus as claimed in claim 1, wherein the gas spring arm unit comprises a fully adjustable gas spring articulating arm unit.

3. The apparatus as claimed in claim 1, wherein the gas spring arm unit further rotates in 360 degrees in a horizontal plane when fitted on the moveable horizontal arm.

4. The apparatus as claimed in claim 1, wherein the predetermined position for the gas spring arm unit is achieved by fixing a first screw over the horizontal arm.

5. The apparatus as claimed in claim 4, wherein the horizontal rod comprises a socket, wherein the socket is configured to achieve at least one of the x-axis, y-axis, z-axis direction in the space for attaining a required position of the endoscope.

6. The apparatus as claimed in claim 1, wherein the rail slider comprises a rack and pinion slider.

7. The apparatus as claimed in claim 1, wherein the rail slider is further configured to move the endoscope in forward and backward direction in the space mechanically with a pinion screw, wherein the pinion screw is horizontally attached to an upper portion of the rail slider.

8. The apparatus as claimed in claim 1, wherein the clamp is configured to hold the endoscope by one of neck and shaft.

9. The apparatus as claimed in claim 1, wherein the holding tube comprises one of a movable holding tube attached with the second ball of the vertical rod and the socket joint and a fixed holding tube by tightening the screw.

10. The apparatus as claimed in claim 1, wherein the rail slider comprises a motor, wherein the motor is moving the rail slider in the forward and backward direction.

* * * * *